United States Patent [19]
Mirell

[11] 4,241,728
[45] Dec. 30, 1980

[54] METHOD AND APPARATUS FOR DISPENSING RADIOACTIVE MATERIALS

[76] Inventor: Stuart Mirell, 10816 Cushdon Ave., Los Angeles, Calif. 90064

[21] Appl. No.: 963,690

[22] Filed: Nov. 27, 1978

[51] Int. Cl.² ............................................. A61N 5/12
[52] U.S. Cl. .................................. 128/1.1; 128/215; 250/506
[58] Field of Search .................. 128/1.1, 215; 250/506

[56] References Cited

U.S. PATENT DOCUMENTS

| | | | |
|---|---|---|---|
| 3,655,981 | 4/1972 | Montgomery et al. | 128/1.1 X |
| 3,669,093 | 6/1972 | Sauerwein et al. | 128/1.1 |

FOREIGN PATENT DOCUMENTS

1466774  7/1973  Fed. Rep. of Germany ............ 128/1.1

OTHER PUBLICATIONS

"Handling of Radioactive Gold for Therapeutic Purposes", Nucleonics, vol. 10, No. 3, Mar. 1952.

*Primary Examiner*—John D. Yasko
*Attorney, Agent, or Firm*—Fulwider, Patton, Rieber, Lee & Utecht

[57] ABSTRACT

A shielded radioisotope injector device and a related method for its use. A conventional, unshielded hypodermic syringe is provided with a bypass insert between the syringe and needle, and a flexible tube coupled to the bypass insert provides an extended-length path from the needle to the syringe, most of the tube being contained within a shielded container. The radioisotope is drawn into the tube after an inert solution, such as saline, is first drawn in, then a further quantity of the inert solution is drawn in, to move the radioisotope totally into the shielded portion of the tube. Administration of the radioisotope as an intravenous injection, including pre- and post-injections of saline, is effected by driving the stored material into a patient's bloodstream.

13 Claims, 3 Drawing Figures

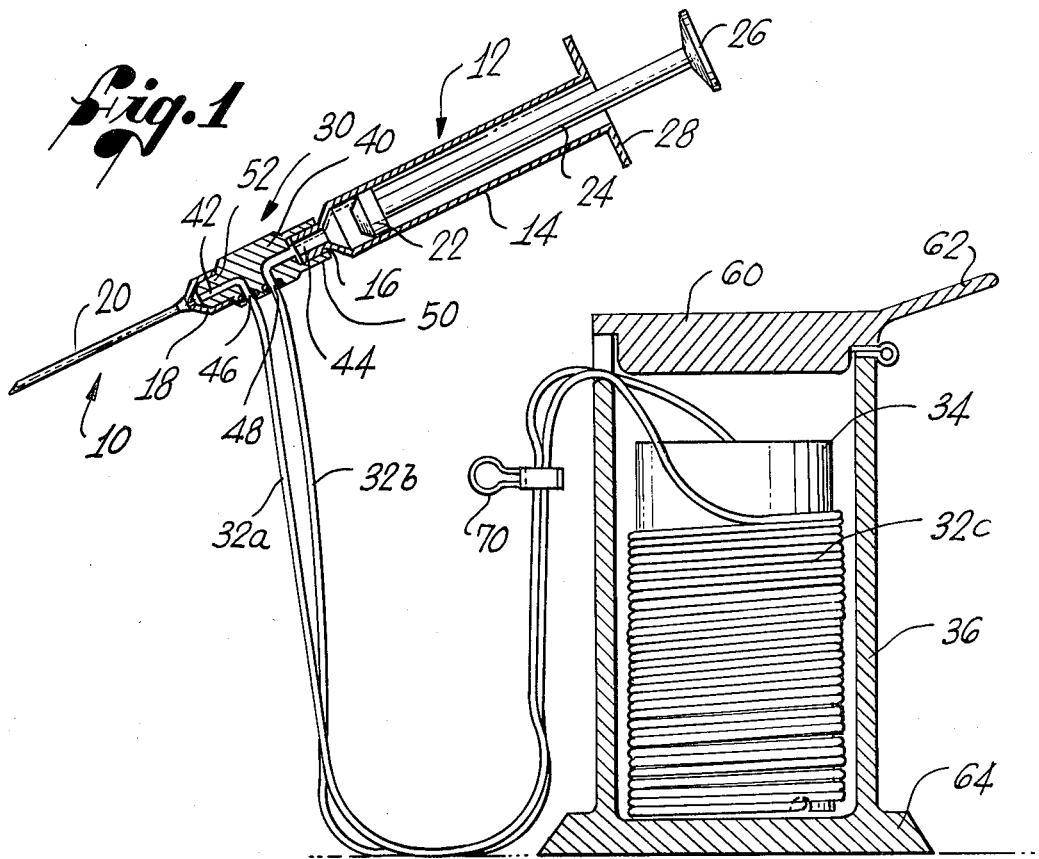
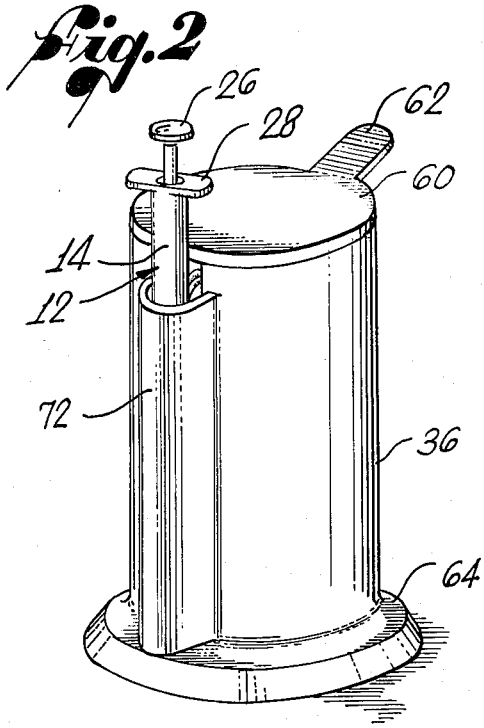
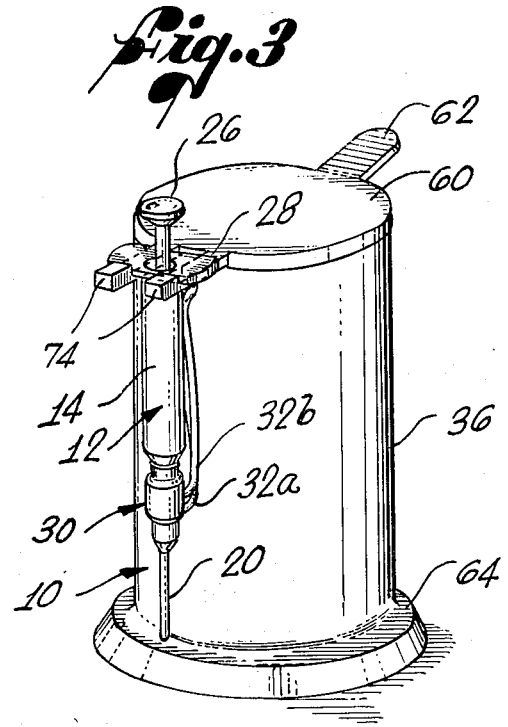

METHOD AND APPARATUS FOR DISPENSING RADIOACTIVE MATERIALS

BACKGROUND OF THE INVENTION

This invention relates generally to systems for dispensing radioactive materials in liquid form, and, more particularly, to hypodermic devices for injecting radioactive materials into a patient, usually for diagnostic purposes.

Radiopharmaceuticals utilized for such purposes emit highly penetrating gamma rays. The flow and distribution of these injected radiopharmaceuticals within organs and blood vessels are imaged by electronic gamma cameras. Although the harmful effects of radiation from a single such procedure on a patient are minimal, the cumulative effects of radiation on personnel involved in the preparation and administration of radiopharmaceuticals poses a significant hazard, widely believed to be the principal occupational hazard in diagnostic nuclear medicine. The degree of exposure is sufficiently high that the federal government has authorized the setting of occupational radiation levels ten times higher than those set for the general population. Significantly, studies have shown that over ninety percent of this radiation exposure is received during the handling of syringes used in administering radiopharmaceuticals.

Syringe shields of various designs have been used to provide some degree of protection, but have not been universally accepted. A syringe shield is typically a thick tube, made of lead or tungsten, that surrounds the barrel of the syringe. A narrow leaded glass port in the shield is often included, to permit viewing of the syringe contents. Although the radiation protection benefits of syringe shields are well known, such devices are still not widely accepted for a number of practical reasons relating to the injection process. Most injections are given by venipuncture of a major surface vein in the arm, and the tactile sensation as the hypodermic needle "pops" into a blood vessel is the principal indicator of proper venipuncture. Verification of proper entry into the vein can be obtained if blood is withdrawn when the syringe plunger is pulled back slightly. However, a disproportionately high percentage of patients subjected to nuclear medicine studies have blood vessels that are exceedingly difficult to enter, either because of repeated punctures for conventional medical injections, or because of health-related vascular deterioration. For these patients, the injection process, which for most normal persons might take about fifteen seconds, can easily take as long as a minute.

The difficulty encountered in inserting a hypodermic needle for purposes of a nuclear study is compounded by problems inherent in the use of a shielded syringe. Unfortunately, the weight and bulk of a shielded syringe substantially detract from the tactile sensation needed for proper venipuncture. Moreover, the thick wall of the shield necessitates injection at a substantially steeper angle than would otherwise be appropriate and desirable, and the needle is, therefore, more likely to penetrate the far wall of the blood vessel. The use of a syringe shield also results in a higher incidence of extravasation, i.e., injection into tissue outside the blood vessel. In addition to these problems, the reduced manipulative ability inherent in the use of a syringe shield increases the time required for proper venipuncture, and thereby reduces, to some degree, the benefits derived from the shielding.

Another drawback relating to syringe shields is that they are effective only when used with radiopharmaceuticals emitting low-energy gamma rays. When radiopharmaceuticals emitting high-energy gamma rays are used, the radiation passes virtually unchecked through the shield, resulting in substantially more radiation exposure. A number of important radiopharmaceuticals currently in use emit radiation at these relatively high energy levels. Many imaging studies must be completed within minutes after injection, and even those studies that require the acquisition of subsequent images, to examine metabolic utilization of the injected material, rarely require images more than several hours after injection. Consequently, the high-energy, short-lived radiopharmaceuticals are ideal for most imaging applications. The use of short-lived isotopes has permitted the dose of the injected radiopharmaceutical to be drastically increased, thereby improving the image quality without increasing the total patient radiation exposure. However, the radiation exposure to personnel who handle the syringes on a continuing basis is proportionately increased. Many of the short-lived radiopharmaceuticals used are positron emitters that are so energetic that a conventional syringe shield is rendered almost totally ineffective.

Another important aspect of nuclear imaging relates to the precise manner in which a radiopharmaceutical is injected. In obtaining images of various organs, it is often critical to obtain information concerning the hemodynamic flow patterns in the organs during the first minute or so following the injection. This technique, known as nuclear angiography, can be employed only if the radiopharmaceutical is injected in a compact concentration, known as a bolus. Unfortunately, an intravenously injected fluid normally tends to diffuse substantially before reaching the imaged organ, thereby resulting in a pronounced loss of sharpness in the resulting nuclear angiogram. Sometimes tourniquets and pressure cuffs are used on the upper arm in an attempt to hold the radioisotope in a bolus until the syringe contents have been completely injected.

In another technique, pre- and post-injections of saline are used to surround the radioisotope as it travels through the blood vessels. The principal diffusion then occurs between the saline and the blood, leaving the centrally located radioisotope in a relatively tight bolus. The saline technique is not widely used, however, because it requires multiple syringes, and a valve to switch the needle from one syringe to another. Moreover, the procedure for injecting saline before and after the radiopharmaceutical is necessarily more awkward, and demands more skill than a conventional injection.

It will be appreciated from the foregoing that there is a significant problem in injecting radiopharmaceutical materials into patients without exposing the personnel preparing and administering the materials to a substantial risk of radiation exposure. While syringe shields provide some degree of protection from low energy radioisotopes, at the cost of impaired facility of injection, there is essentially no technique available to protect personnel from radiation from the short-lived, higher energy radioisotopes. Ideally, what is required is a hypodermic device that retains the manipulative facility of an unshielded syringe, and yet eliminates substantially all radiation exposure in the procedures for preparing and injecting the materials. The present invention satisfies this ideal.

SUMMARY OF THE INVENTION

The present invention resides in apparatus, and a related method, for storing and dispensing radioactive materials with practically no radiation exposure to personnel who operate the apparatus. In the sense that it relates to the nuclear medicine field, the invention resides in a radioisotope injector system and needle, but at the same time protecting personnel from radiation exposure prior to and during the administration of an injected radiopharmaceutical dose. Basically, and in general terms, the injector system of the invention comprises fluid bypass means connectable between a syringe and needle of a conventional hypodermic device, the bypass means having a first port communicating with the syringe and a second port communicating with the needle, and also includes a length of continuous tubing connected between the two ports. A major portion of the tubing is stored within a shielded container, which serves to provide complete radiation protection from personnel handling radiopharmaceutical materials prior to and during administration to a patient.

More specifically, the tubing is preferably of a flexible and transparent material, and most of the tubing is wound onto a cylindrical form housed within the shielded container. Only a few inches of the end portions of the tube extend from the shielded container for attachment to the bypass means.

In use, the syringe is first employed to draw in a quantity of inert fluid, such as a saline solution, through the needle, through the tube, and into the syringe itself. Air trapped within the syringe is then expelled, along with excess saline, and the needle is then placed in the radiopharmaceutical material and the syringe is again actuated to draw in a desired amount of the material. Most of the radiopharmaceutical material drawn in is contained in that portion of the tubing within the shielded container, except for a small volume contained in the needle itself, and in the short length of the tubing communicating directly with the needle and extending to the container. An additional quantity of saline solution is immediately drawn in, to move the radiopharmaceutical material entirely within the shielded container. When the material is to be injected into the patient, the hypodermic needle is properly inserted, without the impediment of a shield around the syringe, and sufficient saline within the syringe is expelled to drive the entire dose of the radiopharmaceutical into the patient. Not only does this procedure minimize exposure to radiation, but it also provides maximum manipulative ability of the hypodermic syringe and needle, and provides a desired bolus injection without the need for multiple syringes.

It will be appreciated from the foregoing that the present invention represents a significant advance in the field of radioisotope injection systems. In particular, it provides a device that retains the manipulative facility of an unshielded syringe, and yet eliminates practically all radiation exposure prior to and during the injection procedure. Other aspects and advantages of the invention will become apparent from the following more detailed description, taken in conjunction with the accompanying drawings.

BRIEF DESCRIPTION OF THE DRAWINGS

FIG. 1 is a cross-sectional view of the injector system of the present invention;

FIGS. 2 and 3 are perspective views of alternate forms of the injector system, incorporating syringe retaining devices.

DESCRIPTION OF THE PREFERRED EMBODIMENT

As shown in the drawings for purposes of illustration, the present invention is principally concerned with improved injector systems of the hypodermic syringe type, for injecting radioisotopes directly into the bloodstream of a patient for diagnostic purposes. As shown in FIG. 1, a conventional hypodermic syringe typically comprises a needle portion, indicated by reference numeral 10, and a syringe portion 12. The syringe portion 12 comprises a cylindrical barrel 14 having a reduced-diameter forward end portion 16 that forms the male element of a coupling, of which the female element 18 is formed integrally with the needle portion 10. The needle portion 10 has a needle 20 with a bore along its length, the bore terminating at the needle point. Fitted inside the barrel 14 is a piston or plunger 22 to which is attached an actuating rod 24. To facilitate operation of the syringe 12, the rod 24 and barrel 14 have integral flanges 26 and 28 respectively at their ends.

As is well known, a syringe of this type is operated by inserting the needle 20 in the fluid to be injected, withdrawing the plunger 22 along the barrel 14 to draw up liquid through the needle and into the syringe barrel 14. After the needle 20 is withdrawn from the liquid supply, the plunger 22 is pushed back into the barrel 14 a sufficient amount to remove air bubbles from the barrel and needle, and to obtain the correct volume or dose within the barrel. Then the needle 20 is inserted into the patient, and the syringe plunger 22 is again actuated to drive the dose into the patient. When the material to be injected is a radioisotope, as is used in a large number of diagnostic procedures, personnel preparing and administering the materials are continually subjected to high levels of radiation, and various techniques have been devised to shield such personnel from the radiation. Typically the prior art techniques have not been successful or even widely accepted, for reasons already discussed.

In accordance with the present invention, the needle portion 10 and syringe portion 12 are interconnected by a bypass insert 30, which provides for the insertion of a long flexible tube 32 in the fluid path between the needle portion 10 and syringe portion 12 of the hypodermic device. The tube 32 may be considered to comprise a first end portion 32a connected to the bypass unit 30 and communicating directly with the bore of the needle 20, and a second end portion 32b also connected to the bypass insert and communicating directly with the inside of the barrel 14, and a long intermediate portion 32c. The intermediate portion 32c is wound in helical fashion onto a rigid cylindrical form 34, which is housed within a shielded container 36.

The bypass insert 30 comprises a generally cylindrical body portion 40 having two passageways 42 and 44, extending one from each end of the body towards the center thereof, and then curving outwardly to terminate in two respective ports 46 and 48, to which the ends of the tube portions 32a and 32b are coupled. The body 40 has an integral female coupling 50 at one end, adapted to couple with the male coupling 16 on the syringe 12, and has an integral male coupling 52 at its other end to couple with the female coupling 18 on the needle portion 10 of the hypodermic syringe. These male and female couplings can be of the conventional hypodermic syringe type, such as Leur fittings or either the Leur slip or the Leur lock type. Alternatively, the bypass unit 30 can be fabricated integrally with either the syringe portion 12, the needle portion 10, or both. In any event, the bypass unit 30 and the tube 32 are preferably disposable items, constructed from medical grade plastic, rubber or latex material. As in conventional hypodermic syringes, the needle portion 10 and the syringe portion 12 are also preferably disposable items.

The tubing 32 may be provided already wound onto the vertical coil form 34 and bonded thereto with an adhesive. Alternatively, the tubing may be provided in an encapsulated or self-fused cylindrical shape without the separate tubular form 34.

For convenience, the container 36 is provided with a hinged lid 60 having an integral thumb-operated lever 62, so that the container may be easily carried and opened with one hand, and a relatively broad and heavy base 64, to ensure stability as the dose is administered.

The injector system of the invention is loaded in such a manner as to place the radioisotope material entirely within the intermediate tube section 32c contained within the shielded container 36. The first step preparing a dose of such material is to draw into the tube, and into the syringe, an inert solution, such as saline. Excess saline is then forced from the syringe in order to remove any air bubbles trapped in the syringe and tube. For relatively small syringes, priming the tube in this manner until all air bubbles are removed may require several operations of the syringe plunger 22.

After removal of all trapped air, the plunger 22 is again drawn back, with the needle 20 this time inserted in the radiopharmaceutical material. The radiopharmaceutical is drawn in through the needle, through the bypass unit 30 and into the end portion 32a of the tube and the intermediate portion 32c. Finally, the needle 20 is again placed in the saline solution, and a further quantity is drawn in through the needle and into the end portion 32a of the tube, until the radiopharmaceutical is drawn entirely into the shielded intermediate portion 32c of the tube. It will be appreciated, then, that there is a small risk of radiation exposure from the material temporarily stored in the end portion 32a of the tube before it is drawn all the way back into the shielded portion 32c of the tube. This exposure can be minimized, however, if the length of the tube end portion 32a is kept as short as possible during the dose preparation phase. This presents no difficulty because the dose preparation phase does not require the same degree of manipulative facility of the syringe and needle as the injection phase. When the dose is being administered, the end portions 32a and 32c of the tube 32 may be withdrawn to a greater extent from the shielded container 36. To minimize dispersion of the radioisotope into the saline solution, tube clamps 70 may be provided on tube portions 32a and 32b immediately outside the shielded container 33.

During dose preparation, the intermediate section of tube 32c can be lifted out of the shielded container 36 in order to verify that the appropriate dose has been loaded. The tube is lifted from the container 36, suspended on the tube end portions 32a and 32b, and placed in a conventional electronic dose calibrator (not shown). It can then be returned back to the safety of the shielded container with a minimum of radiation exposure.

To facilitate handling of the improved device, means may be provided to retain the entire syringe assembly, with tube 32 attached, in close proximity to the container 36. As shown in FIGS. 2 and 3 by way of example, this retaining means can take the form of a cylindrical sheath 72 integral with the walls of the container, or a pair of retaining brackets 74 engaging the syringe flange 28.

In accordance with an important aspect of the invention, the injected radioisotope is retained in a relatively tight bolus between the preceding and following injections of saline solution. For most procedures, this is a desirable technique for administering the radioisotope, and is here obtained without the necessity of multiple syringes and switching valves.

It will be appreciated from the foregoing that the present invention represents a significant step forward in the field of nuclear medicine, and in the preparation and administration of doses of radioisotopes. In particular, it allows venipuncture to be performed with the same convenience as in the administration of a non-radioactive material, and yet provides essentially complete protection from radiation. It will also be appreciated that, although a specific embodiment of the invention has been described in detail for purposes of illustration, various modifications may be made without departing from the spirit and scope of the invention. Accordingly, the invention is not to be limited except as by the appended claims.

I claim:

1. Apparatus for use with a device for dispensing radioactive liquids in predetermined amounts, the device having dispensing means and reservoir and pump means connected thereto for drawing in, temporarily retaining, and pumping out liquid through the dispensing means, said apparatus comprising:

bypass means connectable between the dispensing means and the reservoir and pump means, to provide an extended-length liquid path therebetween, said bypass means including liquid storage means locatable remote from the dispensing means and reservoir and pump means;

shielding means surrounding only said liquid storage means of said bypass means, whereby radioactive liquids may be safely stored in said liquid storage means within said shielding means, and dispensed through the dispensing means in a conventional manner, without the need for cumbersome shielding around the dispensing means and reservoir and pump means.

2. Apparatus for use with a device for dispensing radioactive liquids in predetermined amounts, the device having dispensing means and reservoir and pump means connected thereto for drawing in, temporarily retaining, and pumping out liquid through the dispensing means, said apparatus comprising:

bypass means connectable between the dispensing means and the reservoir and pump means, to provide an extended-length liquid path therebetween; and shielding means surrounding a portion of said bypass means, whereby radioactive liquids may be safely stored in said bypass means within said shielding means, and dispensed through the dispensing means in a conventional manner; and wherein said bypass means includes
  a bypass insert having a first port connectable in fluid communication with the dispensing means, and a second port connectable in fluid communication with the reservoir and pump means, and
  a length of continuous tubing having its ends coupled to said first and second ports, respectively, said tubing being contained for the most part within said shielding means.

3. Apparatus as set forth in claim 2, wherein:
said tubing is wound in a coil within said shielding means.

4. For use with a conventional hypodermic syringe and needle, apparatus for injecting radioactive materials with minimal exposure to radiation, said apparatus comprising:
  a bypass insert connectable between the syringe and needle;
  an elongated tube coupled to said bypass insert to provide an extended-length path between the syringe and the needle; and
  a shielded container surrounding most of the length of said tube, to provide shielded storage for the material prior to injection, without impairing manipulation of the syringe and needle;
  whereby an inert liquid is first drawn into said tube and the syringe, the radioactive material is next drawn in, then a further quantity of inert liquid is drawn in to move the radioactive material entirely into said shielded container.

5. Apparatus as set forth in claim 4, wherein:
said bypass insert includes a body with conventional couplings to connect between the syringe and needle, first and second ports in said body, a first passage for connecting the needle with said first port, and a second passage for connecting the syringe with said second port; and
said tube is connected between said first and second ports.

6. Apparatus as set forth in claim 4, wherein:
said tube is wound as a helical coil within said shielded container.

7. Apparatus as set forth in claim 4, wherein said shielded container includes integral means for retaining the syringe and needle for ease of carrying and handling.

8. A shielded radioiostope injector system, comprising:
  a hypodermic syringe;
  a hypodermic needle;
  a bypass insert connected between said syringe and said needle and having a first port in fluid communication with the bore of said needle, and a second port in fluid communication within said syringe;
  shielded storage means; and
  two lengths of flexible tubing connecting said shielded storage means with said first and second ports, wherein said bypass insert, said tubing and said shielded storage means form a continuous path between said syringe and said needle, whereby a radioisotope can be loaded into said shielded storage means by drawing in a quantity of inert liquid before and after drawing in the radioiostope.

9. A shielded radioiostope injector system as set forth in claim 8, wherein said shielded storage means includes:
  a shielded container; and
  an intermediate length of tubing located in said container and forming a continuous tube with said two lengths of tubing coupled to said first and second ports.

10. A shielded radioisotope injector system as set forth in claim 9, wherein said intermediate length of tubing is wound as a helical coil in said shielded container.

11. A shielded radioisotope injector system as set forth in claim 9, and further including clamping means attached to said two lengths of tubing in proximity to said shielded container.

12. A shielded radioisotope injector system as set forth in claim 9, wherein said shielded container includes integral means for securing said syringe and needle to said container for ease of carrying and handling.

13. A method of loading a radioisotope dose and administering it to a patient, using a hypodermic device having a conventional syringe and needle, a bypass insert and a tube to provide storage in a shielded container coupled between the syringe and needle, said method comprising the steps of:
  drawing a quantity of inert saline solution into the needle, bypass insert, tube and syringe;
  expelling excess saline solution and simultaneously removing trapped air from the syringe and tube;
  drawing a desired amount of the radioisotope into the needle and tube;
  drawing in a further quantity of saline solution to move the radioisotope entirely to a portion of the tube located within the shielded container;
  inserting the needle into the patient; and
  expelling the radioisotope into the patient, together with pre- and post-injections of saline solution.

* * * * *